United States Patent [19]
Brown et al.

[11] Patent Number: 5,769,887
[45] Date of Patent: Jun. 23, 1998

[54] DELIVERY CATHETER AND GRAFT FOR ANEURYSM REPAIR

[75] Inventors: Peter S. Brown, Mountain View; James M Cannon, Jr., Santa Clara; Geoffrey A. Orth, El Granada, all of Calif.

[73] Assignee: Endotex Interventional Systems, Inc., Menlo Park, Calif.

[21] Appl. No.: 785,198

[22] Filed: Jan. 17, 1997

Related U.S. Application Data

[63] Continuation of Ser. No. 336,875, Nov. 9, 1994, abandoned.

[51] Int. Cl.$^6$ .................................................. A61F 2/06
[52] U.S. Cl. ................................ 623/1; 623/12; 606/194; 606/195; 606/198
[58] Field of Search .................. 623/1, 12; 606/194, 606/195, 198

[56] References Cited

U.S. PATENT DOCUMENTS

| | | | |
|---|---|---|---|
| 3,657,744 | 4/1972 | Ersek | 3/1 |
| 4,562,596 | 1/1986 | Kornberg | 623/1 |
| 4,580,568 | 4/1986 | Gianturco | 128/345 |
| 4,617,932 | 10/1986 | Kornberg | 128/334 |
| 4,733,665 | 3/1988 | Palmaz | 606/108 |
| 4,787,899 | 11/1988 | Lazarus | 623/1 |
| 4,830,003 | 5/1989 | Wolff et al. | 128/343 |
| 4,872,874 | 10/1989 | Taheri | 623/1 |
| 4,994,071 | 2/1991 | MacGregor | 606/194 |
| 5,035,706 | 7/1991 | Gianturco et al. | 606/198 |
| 5,078,726 | 1/1992 | Kreamer | 606/194 |
| 5,104,399 | 4/1992 | Lazarus | 623/1 |
| 5,104,404 | 4/1992 | Wolff | 623/1 |
| 5,135,536 | 8/1992 | Hillstead | 606/195 |
| 5,195,984 | 3/1993 | Schatz | 606/195 |
| 5,207,695 | 5/1993 | Trout, III | 606/153 |
| 5,211,683 | 5/1993 | Maginot | 128/898 |
| 5,219,355 | 6/1993 | Parodi et al. | 606/191 |
| 5,275,622 | 1/1994 | Lazarus et al. | 623/1 |
| 5,282,824 | 2/1994 | Gianturco | 606/198 |
| 5,282,846 | 2/1994 | Schmitt | 623/1 |
| 5,282,847 | 2/1994 | Trescony et al. | 623/1 |
| 5,282,848 | 2/1994 | Schmitt | 623/1 |
| 5,316,023 | 5/1994 | Palmaz et al. | 128/898 |
| 5,360,443 | 11/1994 | Barone et al. | 623/1 |
| 5,383,892 | 1/1995 | Cardon et al. | 606/198 |
| 5,397,345 | 3/1995 | Lazarus | 623/1 |

FOREIGN PATENT DOCUMENTS

| | | |
|---|---|---|
| 91304988 | 6/1991 | European Pat. Off. . |
| 91308991 | 10/1991 | European Pat. Off. . |
| 91309197 | 10/1991 | European Pat. Off. . |
| 92309777 | 10/1992 | European Pat. Off. . |
| 0621016 | 10/1994 | European Pat. Off. . |
| 1457921 | 2/1989 | U.S.S.R. . |

*Primary Examiner*—Paul B. Prebilic
*Attorney, Agent, or Firm*—Fish & Neave; Nicola A. Pisano

[57] ABSTRACT

This invention provides a graft delivery system and methods for its use comprising a prosthetic graft secured to an expandable anchoring member, such as a stent, by a butt-joint attachment means to minimize the system's profile. The delivery system employs a catheter with a relatively small diameter shaft for flexibility and a relatively large diameter delivery base for supporting expansion of the anchoring member. The butt-joint attachment means comprises any means suitable to secure the graft to the anchoring member when deployed within the patient's vasculature and allows the anchoring member and graft to expand during deployment. In a preferred embodiment, the delivery system is configured so that the expansion of the anchoring member pulls the distal end of the graft over the proximal end of the anchoring member and the final expansion of the anchoring member seals the distal end of the graft between the proximal end of the anchoring member and the vessel. One preferred method of use is to deploy a second anchoring member coaxially within the already deployed first anchoring member and graft assembly, overlapping at least the distal end of the graft in order to further secure the graft and minimize flow by.

14 Claims, 6 Drawing Sheets

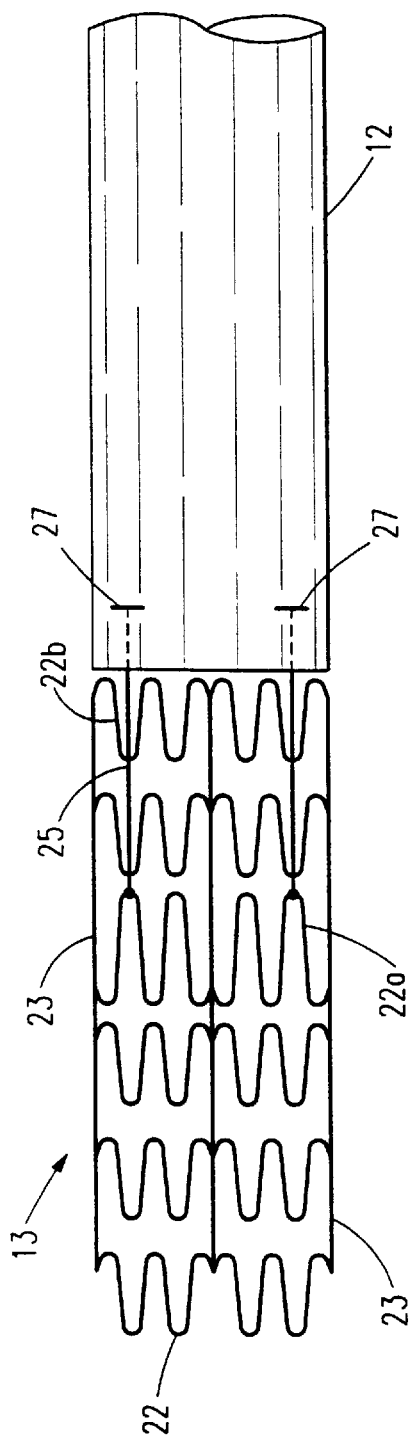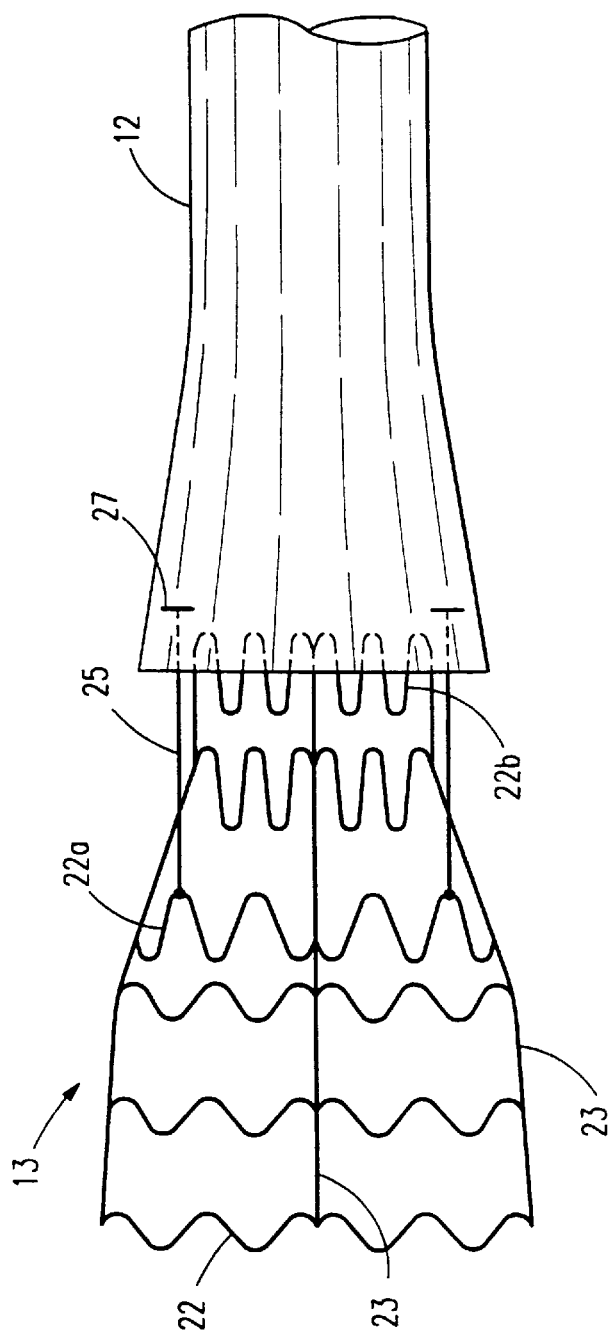

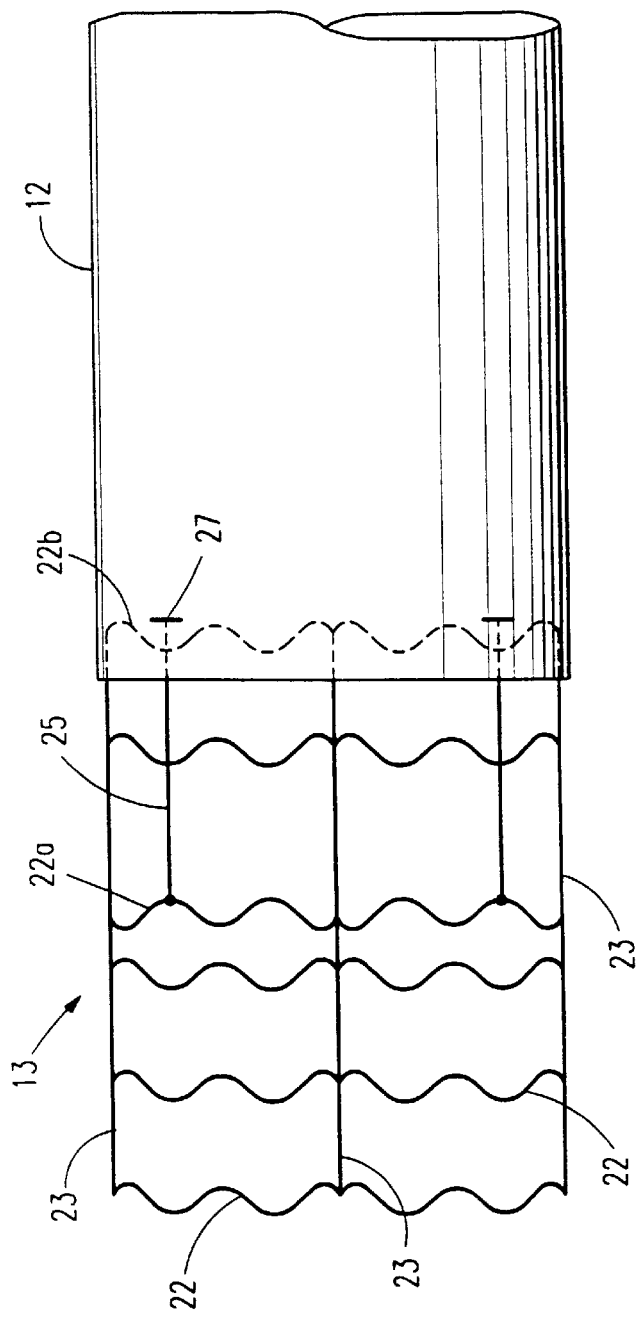
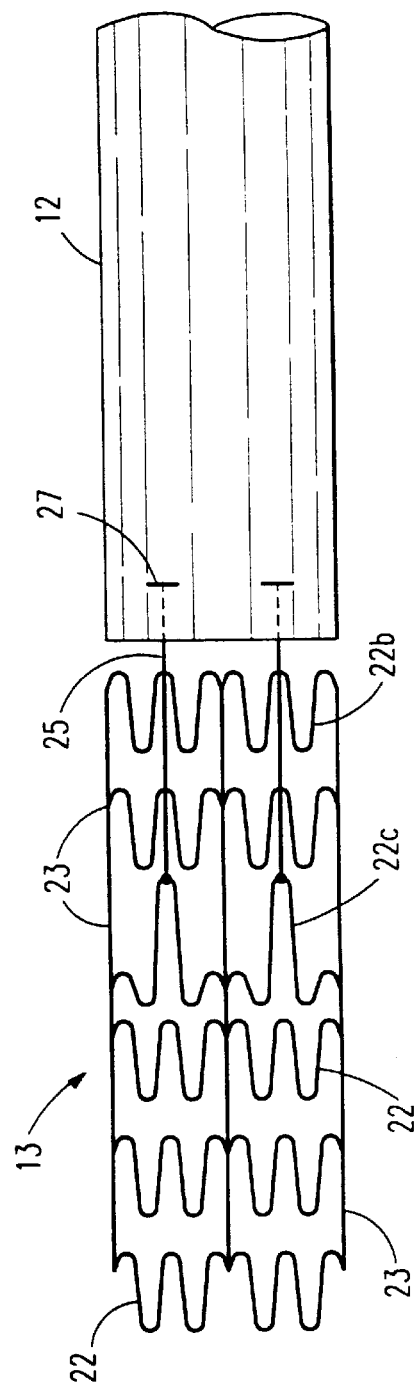

DELIVERY CATHETER AND GRAFT FOR ANEURYSM REPAIR

This application is a continuation of U.S. patent application Ser. No. 08/366,875, filed Nov. 9, 1994, entitled DELIVERY CATHETER AND GRAFT FOR ANEURYSM REPAIR, abandoned.

BACKGROUND

This invention relates to the delivery and placement of vascular grafts, and in particular, to a method and system for the repair of abdominal aortic aneurysms.

An aneurysm is a sac resulting from abnormal dilation of the artery wall and is often associated with arteriosclerotic disease. Unless treated, an aneurysm can rupture, leading to severe and often fatal hemorrhaging. Treating an aortic aneurysm generally involves transplanting a prosthetic graft to bridge the affected section of the aorta. Surgical implantation of the graft is possible but this treatment causes considerable trauma, results in high mortality and morbidity and, even when completely successful, requires a lengthy recuperation period. Due to the difficulty of the operation, direct surgical replacement is even less attractive when it must be performed on an emergency basis after the aneurysm has ruptured.

A less invasive alternative involves the use of a catheter to effect intraluminal delivery of a graft. Prior art graft delivery systems, such as disclosed in EP 0 461 791; A1 (Barone et al.), employ a graft with expandable portions that anchor the graft in the aorta. Often, the systems use an inflatable balloon on the delivery catheter to expand the anchoring portion of the graft as disclosed in U.S. Pat. No. 5,275,622 (Lazarus et al.) which is hereby incorporated in its entirety by reference thereto. This latter example requires the use of a bulky capsule to store the graft and a complicated pushrod system to deploy the graft.

The success of a percutaneous vessel repair depends in large part on getting the graft to the location of the vasculature in need of repair and deploying the graft effectively. A difficulty associated with graft deployment is blood flow-by which occurs when blood can pass between the graft and the patient's vessel, bypassing the graft.

Although the referenced prior art systems and others employ many different stent and graft configurations, none are completely satisfactory. The principle limitation of the prior art systems is their size. They typically require a delivery catheter having a diameter of approximately 28–30 French (9.3 to 10 mm). Although it is desirable to introduce grafts through the femoral artery, its inner diameter is only about 4 to 6 mm. Thus, the size of the prior-art devices restricts them to introduction through upper femoral sites, where access may be difficult. Further, these systems are too bulky and inflexible to access many regions of a patient's vasculature. Accordingly, there is a need for a delivery catheter and graft system capable of introduction through a smaller opening while maintaining the ability to reliably and securely deploy the graft.

SUMMARY OF THE INVENTION

This invention provides a method and graft delivery system which minimizes the system's profile to aid its placement and to permit access to more areas of a patient's vasculature. The system generally comprises a prosthetic graft secured to an expandable anchoring member, such as a stent, by a butt-joint attachment means. The delivery system employs a catheter with a relatively small diameter flexible shaft and a relatively large diameter delivery base to support expansion of the anchoring member.

The graft is attached to the anchoring member in a suitable manner and the anchoring member and graft assembly are loaded on the delivery catheter in a precise configuration to minimize the system's profile. Since anchoring members have a finite degree of expansion, an anchoring member which has an expanded diameter large enough to be securely deployed within a given vessel has a minimum diameter corresponding to the anchoring member's most compressed state. To effectively expand the anchoring member, the delivery system must have a diameter large enough to support the anchoring member in its most compressed state. Accordingly, the catheter comprises a delivery base having a means to expand the anchoring member and a diameter which approximates the anchoring member's minimum compressed diameter to support the anchoring member during deployment. The remainder of the catheter shaft has a smaller diameter than the delivery base to provide flexibility. The anchoring member and graft are coaxially threaded over the delivery catheter and positioned with the anchoring member over the delivery base and the graft over the catheter shaft just proximal to the delivery base. In order to minimize the system's profile, the graft does not overlap the delivery base because its effective wall thickness is much greater than the anchoring member's. Accordingly, the anchoring member and graft have a butt-joint attachment prior to deployment to avoid overlap between the graft and the delivery base.

The butt-joint attachment means comprises any means suitable to secure the graft to the anchoring member when deployed within the patient's vasculature and allows the anchoring member and graft to expand during deployment. The attachment also minimizes the flow by of blood once the graft and anchoring member are deployed. In a preferred embodiment, the delivery system is configured so that the expansion of the anchoring member pulls the distal end of the graft over the proximal end of the anchoring member and the final expansion of the anchoring member seals the distal end of the graft between the proximal end of the anchoring member and the vessel. In other embodiments, a plurality of staples extend from the anchoring member and attach the graft via hooks, T-bars, or the like. Alternatively, a plurality of ribbons extending from the graft are woven through the anchoring member. This invention also comprises the method of deploying a second anchoring member within the deployed graft and first anchoring member to overlap at least the upstream edge of the graft, securing and sealing the graft within the vessel to minimize or prevent flow by.

The graft delivery systems of this invention provide a means for attaching the graft to the anchoring member and a delivery catheter which minimize the profile of the system. While the invention has been described primarily with respect to a system comprising the catheter loaded with an anchoring member and graft, it includes the delivery catheter alone, kits which include unassembled catheters, anchoring members and grafts, and methods of use.

BRIEF DESCRIPTION OF THE DRAWINGS

FIGS. 4a–c illustrate a prosthetic assembly of the invention having a graft overlapping attachment of the anchoring member, showing the compressed, expanding and expanded states, respectively. FIG. 4d illustrates an alternate embodiment of the anchoring member.

DETAILED DESCRIPTION OF THE INVENTION

Figure 1:
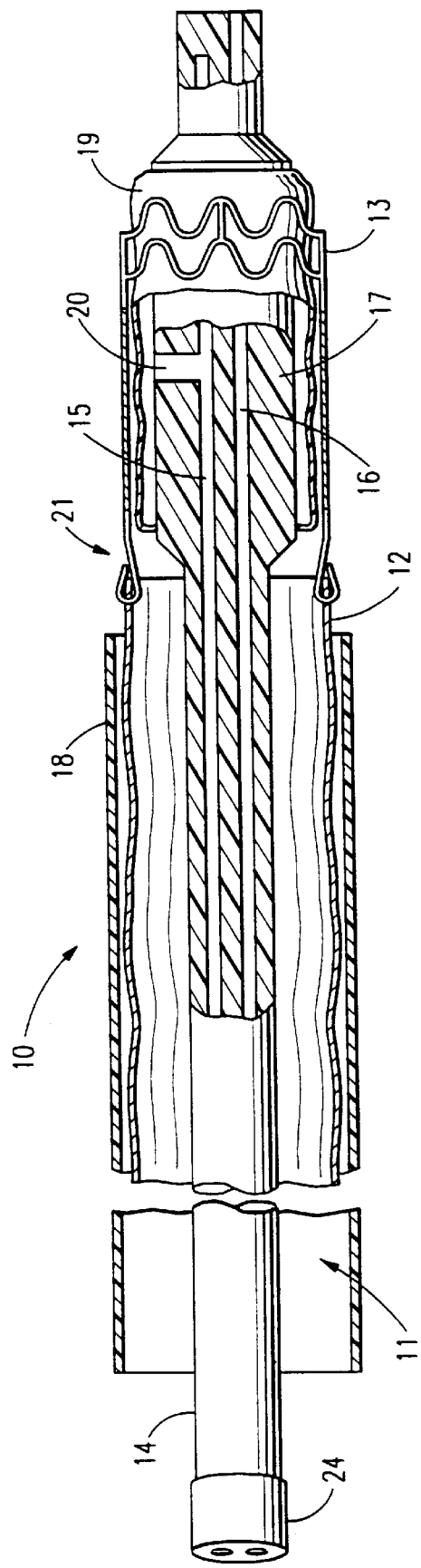
FIG. 1 is a longitudinal cross-sectional view of a delivery catheter and graft system embodying features of this invention.
Figure 3A:
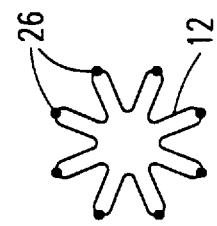
FIG. 3a is transverse cross-sectional view of graft and attachment taken at a—a.

FIG. 1 is a elevational view in section illustrating a catheter system 10 embodying features of the invention which generally comprises a catheter 11 with an aortic graft 12 attached to an expandable anchoring member, stent 13, loaded for delivery. The catheter 11 comprises a flexible catheter shaft 14 with proximal and distal ends, an inflation lumen 15 and a guidewire lumen 16. A delivery base 17 is located on a distal portion of the catheter shaft 14 and has a substantially larger outer diameter than the adjacent catheter shaft 14. A thinwalled retractable sheath 18 is slidably disposed over the catheter 11 and configured so that it can cover the scent 13 and attached graft 12 during introduction and placement of the catheter system 10 and be withdrawn once they are in an appropriate position within the patient.

In this embodiment, the means for expanding stent 13 comprises an inflatable balloon 19 positioned over delivery base 17 and in fluid communication with the inflation lumen 15 through inflation passage 20, but other means or the use of a self-expanding anchoring member are suitable.

The distal end of the graft 12 is secured the proximal end of stent 13 by a butt-joint attachment means 21. Means of attachment include employing hooks and staples, a graft overlapping anchoring member configuration, graft ribbons or woven wires as discussed below regarding FIGS. 2–7. In general, attachment of graft 12 to stent 13 provides sufficient support to retain the graft 12 at the desired location within a patient's vasculature once stent 13 is deployed. There are also sufficient points of attachment to support the graft 12 in an open position once graft 12 and stent 13 are expanded, helping seal the graft 12 in the vessel and minimizing flow by of blood.

Figure 2A:
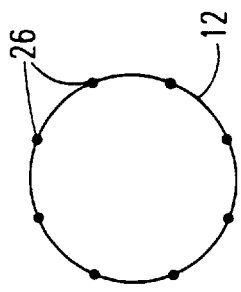
FIG. 2a is transverse cross-sectional view of graft and attachment taken at a—a.
Figure 2:
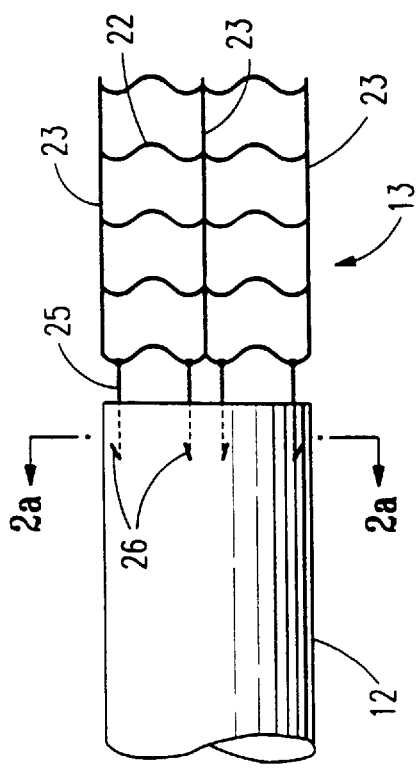
FIG. 2 is an elevational view of a prosthetic assembly of the invention showing the hook and staple attachment of the anchoring member to the graft in their expanded states.
Figure 3:
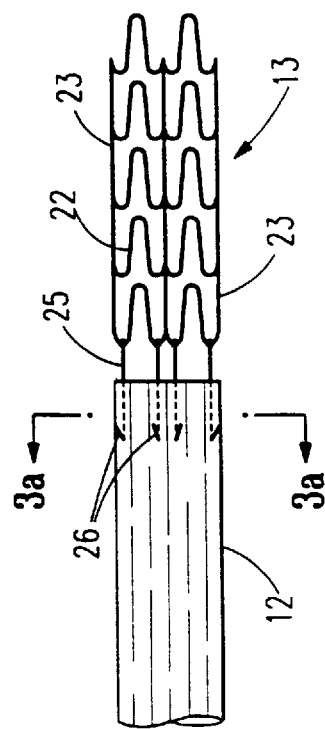
FIG. 3 is an elevational view of a prosthetic assembly of the invention showing the hook and staple attachment of the anchoring member to the graft in their compressed states.

As shown in FIGS. 2–3, the effective wall thickness of stent 13 does not change between the pre-expanded and expanded states. On the other hand, the graft 12 bunches when compressed to conform to the catheter shaft 14 and forms overlaps and pleats, effectively increasing its wall thickness as shown in FIG. 4a. stent 13 and graft 12 are coaxially threaded over the catheter 11 so that stent 13 is positioned over the increased diameter delivery base 17 and the graft 13 is positioned over the narrow diameter distal section catheter shaft 14 proximal to the delivery base as shown in FIG. 1. Graft 12 and stent 13 have a butt-joint attachment prior to deployment, so that graft 12 does not overlap with the stent 13 or the delivery base 17. Employing a butt-joint attachment between the anchoring member and the graft saves approximately 5.1 mm from the diameter of system 10 over conventional systems. Accordingly, the delivery catheters of this invention have an insertion diameter of less than 7 mm and preferably about 6 mm. This allows system 10 to present a small outer diameter for introduction into the body, preferably through the femoral artery, while maintaining the flexibility necessary to pass through tortuous regions of a patient's vasculature.

The diameter of the delivery base 17 should be between about 1.1 and 4.0 times greater than the diameter of the catheter shaft 14 and preferably between about 2.0 to 2.5 times greater in order to provide support for the expansion of stent 13. Generally, the length of the delivery base 17 preferably is at least as long as the inflatable balloon 19 and may be up to two times or more the length of the balloon 19. The balloon 19 may be shorter or longer than the stent 13. In one embodiment, a 5F catheter shaft (1.7 mm) is coupled with a 1 2F delivery base (4 mm) which is about 13 mm longer than the anchoring member.

Preferably, the stent 13 is a Bronco® stent, available from Advanced Cardiovascular Systems, Inc. of Santa Clara, Calif. As shown in FIG. 3, for example, it comprises a framework having a series circular expanding members 22 joined by tie bars 23 to form an open cylinder. The expanding members 22 have a generally sinusoidal shape with the sinusoid forming the wall of the cylinder. When expanded, the diameter of the expanding members 22 increases as the amplitude of the sinusoid flattens out as shown in FIG. 2. As a result of this design, the length of stent 13 does not change substantially when expanded.

Other means of expanding the stent 13 may be employed. Stent 13 could be constructed from shape-memory materials causing it to revert to its expanded shape at body temperatures. In such embodiments, thin-walled sheath 18 would restrain anchoring member 12 until properly positioned.

The proximal end of catheter shaft 14 has a cap 24 bonded the end to provide access to inflation lumen 15 and guidewire lumen 16. The configuration of cap 24 allows it to mate with a multi-arm adaptor (not shown) that supplies inflation fluid and allows guidewire control in a conventional manner. Cap 24 is preferably formed from metal, although other materials such as plastics are suitable. The diameter of cap 24 allows the compressed graft 12 and stent 13 to be threaded over the proximal end of catheter shaft 14, since when graft 12 is compressed, it will not fit over delivery base 17.

FIGS. 2–3 detail the hook and staple butt-joint attachment means 21 of the graft 12 to the stent 13. A plurality of staples 25 extend from the proximal end of the anchoring member and engage the graft with a hook 26 or a T-bar 27 as shown in FIG. 4. Other suitable means for engaging the graft 13 may be located at the end of each staple 25. As shown in FIGS. 2–3, the staples 25 are separate elements which are attached to the proximal end of stent 13 by suitable means, such as welding, bonding or bending the end of each staple 25 around the stent 13. Alternatively, the stent 13 may be configured so that it has integral extensions of the anchoring member shaped in the form the staples which may be use to connect the stent 13 to the graft 12.

FIGS. 4a–c illustrate an alternate, preferred means of attachment. In this embodiment, staples 25 are attached to an expanding member 22a near the proximal end of the stent 13, leaving at least one expanding member 22b more proximal to the graft 12. T-bars 27 at the ends of the staples 25 engage a portion of the distal end of the graft 12. The staples 25 are attached to the portion of the expanding member 22a closest to the graft 12. As depicted in FIGS. 4b-c, the sinusoidal expanding member 22a flattens out during expansion. Since the overall length of the stent 13 does not change during expansion, the distal end of graft 12 is pulled towards and over at least one expanding member 22b at the proximal end of stent 13. The expansion of expanding member 22b acts to seal the opening of the graft 12 to the patient's vessel. In one embodiment, the axial distance between the point of attachment of tie bar 23 and staples 25 to expanding member 24b is 4.45 mm when the stent 13 is compressed. When expanded, this distance is reduced to 2.92 mm. The expansion produces about 1.5 mm of movement to pull distal end of graft 12 over the proximal end of stent 13.

Scent 13 in FIG. 4d illustrates a configuration to maximize the relative motion of the graft 12. Sinusoidal expanding member 22c has varying amplitudes with the greatest amplitude oriented towards the graft 12. Accordingly, the flattening of this sinusoid when stent 13 is expanded pulls the staples 25 a relatively greater distance than expanding members without varying amplitudes.

As shown in FIG. 4b, means for differential expansion expands the distal end of stent 13 before the proximal end. This allows graft 12 to be pulled over expanding member 22b before it expands. In one embodiment, stent 13 is formed so that the proximal portion comprises a heavier gauge material than the distal portion so that the distal portion expands before the proximal portion. In other embodiments, the inflatable balloon 19 may be formed from material of varying resilience so that the distal portion of the balloon expands before the proximal portion. A multi-balloon system allowing sequential expansion may also be employed. Differential expansion in embodiments comprising a self-expanding anchoring member may be achieved in many suitable ways. For example, in embodiments where stent 13 is formed from NiTi alloys, the expanding members 22 could be formed from alloys having slightly different transition temperatures in the distal portion and the proximal portion. Alternatively, the restraining sheath 18 could be withdrawn from the distal portion of stent 13 while still restraining the proximal portion.

Figure 5:
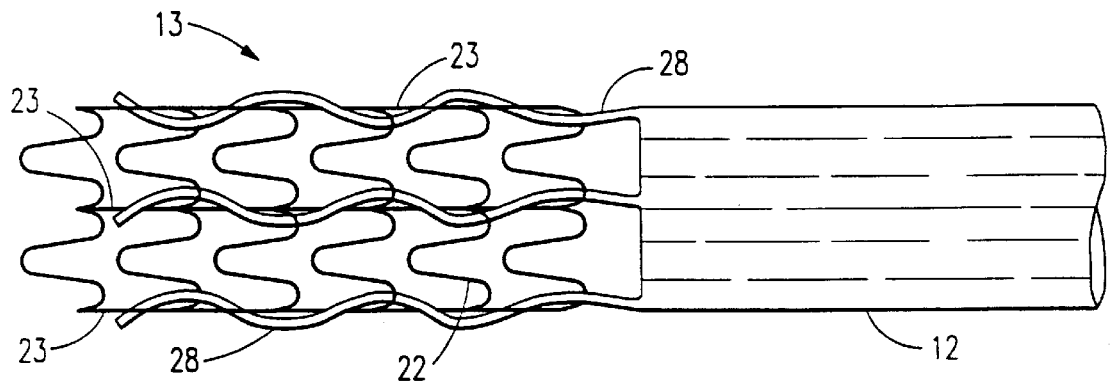
FIGS. 5–6 illustrate prosthetic assemblies of the invention having attachment means employing graft ribbons.
Figure 6:
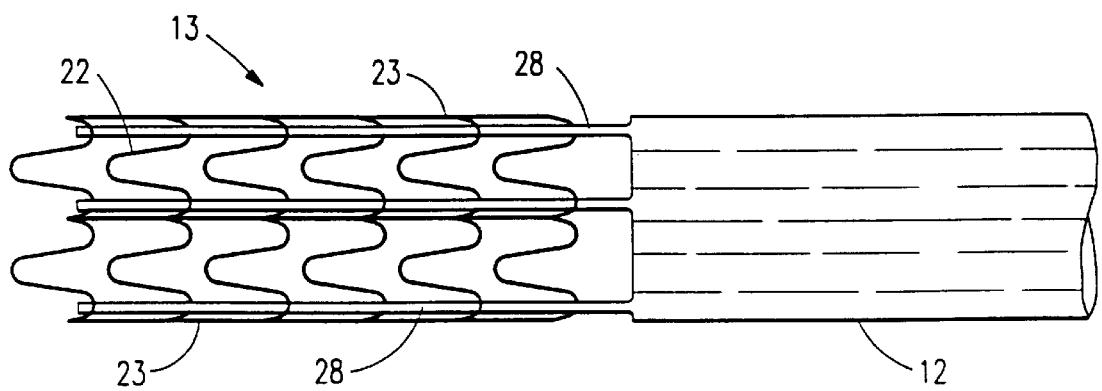
Figure 7:
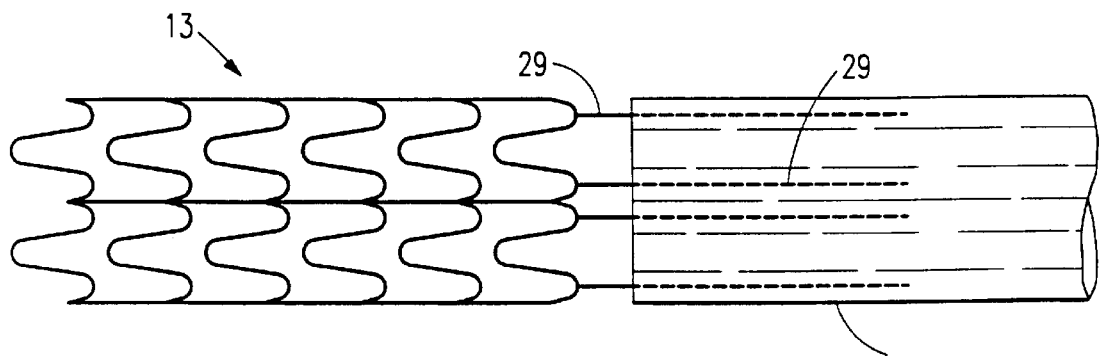
FIG. 7 illustrates a prosthetic assembly of the invention having attachment means employing wires woven into the graft.

FIGS. 5–7 show alternative anchoring member to graft attachments. In FIGS. 6 and 7, portions of the distal end of graft 12 have been removed to leave a plurality of graft ribbons 28 disposed radially around the distal end of graft 12. In FIG. 6, the ribbons 28 are wound around the tie bars 23 of stent 13. In FIG. 7, the ribbons 28 are wound in and out of adjacent expanding members 23 on stent 13. In both situations, only a small portion of graft 12 (the ribbons 28) is used in the attachment, so the overlap of these portions with stent 13 and delivery base 17 when loaded on catheter system 10 does not substantially increase the system's profile. Instead of being integral extensions of the graft, graft ribbons 28 may also be separate elements attached to graft 12 by any suitable means. In FIG. 7, a plurality of wires 29, preferably stainless steel, are woven into graft 12. The free ends of the wires 29 are attached to stent 13 by any suitable means, including welding, soldering, bonding and tying.

The anchoring members may be formed from any suitable material, including tantalum, stainless steel, other metals and polymers and when employing a self-expanding anchoring member, shape-memory metals such as NiTi alloys. The anchoring member may also be coated with a polymer or seeded with endothelial cells to further inhibit thrombosis. Generally, the anchoring member is formed in its pre-expanded state. Once attached to the graft and positioned over the delivery base 17, the anchoring member may be crimped down to a slightly smaller inner diameter to secure the assembly during introduction and to further reduce the delivery diameter. Anchoring member configurations are suitable so long as they are self supporting within the aortic passageway while providing suitable means for attachment to hold the graft in place.

The grafts of this invention are intact tubes, preferably constructed of a synthetic yarn, monofilament or multifilament, formed from materials such as polyesters (including Dacron®), polytetrafluoroethylene (PTFE), polyurethane and nylon. Dacron® in particular, a multifilament composed of polyethylene terephthalate (PET), has been shown to be suitable and may promote formation of intima. The synthetic material may be woven or knit. The woven grafts are generally stronger and less porous while knit grafts are softer and more porous. Additionally, the surface of the synthetic material may be texturized and woven or knit to form a velour surface which generally facilitates growth of tissue from the surrounding lumen through the velour loops to help secure the graft. If desirable, the graft may be bifurcated.

The catheter shaft 14 may be formed from any suitably flexible material, such as pseudoelastic metals (e.g. NiTi alloys) and a wide range of conventional polymers. Preferably, the catheter shaft 14 is formed from an extrudable polymer such as polyethylene (PE). The delivery base 17 may be formed as an integral part of the shaft 14 as shown or may be a separate element which is attached to the shaft in any suitable manner.

The inflatable balloon 19 preferably may be an essentially non-distensible inflatable balloon to provide the degree of expansion control and durability necessary to effectively anchor the anchoring member. The balloon may be formed from any suitable material such as PE, polyethylene terephthalate (PET) or nylon or other polyamide.

The use of the catheter system 10 generally follows conventional procedures. In particular, a guidewire (not shown) is backloaded into guidewire receiving lumen 16 of the catheter 11 with sheath 18 extending over the compressed and loaded graft 12 and attached stent 13. The catheter system 11 and guidewire are percutaneously introduced by means of conventional cut down techniques in the patient's arterial system, generally through the femoral artery. The guidewire is advanced out delivery catheter 11 and up the aorta via fluoroscopic imaging until it crosses the aneurysm. Then the catheter 11 is advanced over the guidewire until the stent 13 is positioned within the aorta adjacent to healthy tissue upstream from the aneurysm. The sheath 18 is retracted to expose the stent 13 and the graft 12. The balloon 19 is inflated to expand the stent 13 to anchor it in the aorta. The balloon 19 is then deflated and the catheter 11 is removed, leaving the anchored anchoring member and graft in place.

Figure 8:
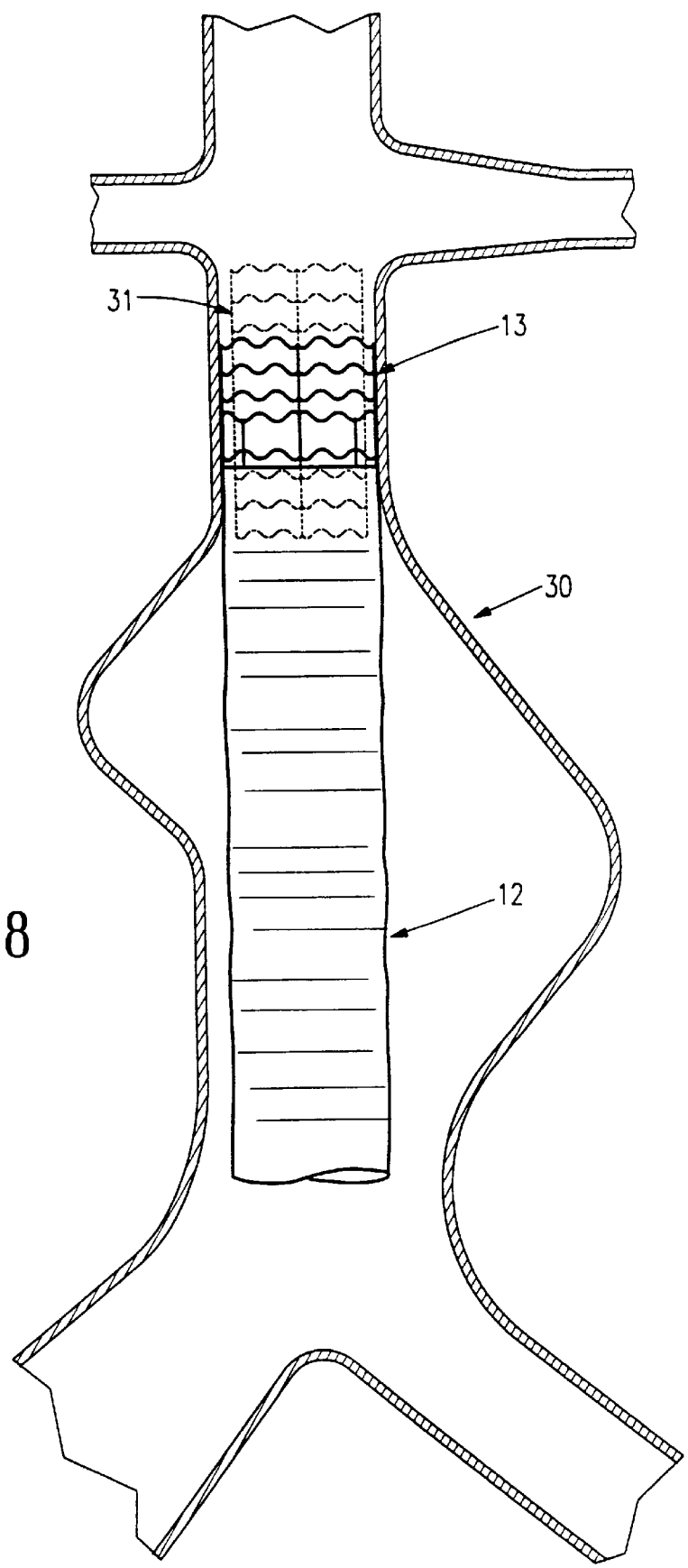
FIG. 8 illustrates a method of the invention using a second anchoring member to further seal and secure the graft.

Once deployed, the attachment of the graft to the anchoring member and the sealing of the graft to the patient's vessel may be improved by deploying a second anchoring member as illustrated in FIG. 8. Once the first stent 13 and attached graft 12 are deployed within a patient's vessel 30, a second anchoring member 31 without an attached graft is deployed coaxially within the stent 13 and graft 12. The second anchoring member overlaps the attachment between first stent 13 and graft 12 to sandwich the graft 12 against the vessel, further minimizing flow by. Preferably, the second anchoring member 31 is approximately two times the length of the first stent 13 and extends past the distal end of the first stent 13.

The invention has been described herein primarily with reference to presently preferred embodiments. However, it should be recognized that various modifications and improvements can be made to the invention without departing from the scope thereof.

What is claimed is:

1. A graft delivery system comprising:
   a) a catheter having an elongated shaft and a delivery base on a distal portion of the elongated shaft;
   b) a graft having proximal and distal ends, the graft mounted in a compressed state on the elongated shaft;
   c) an anchoring member mounted on the delivery base and having proximal and distal ends, first and second expanding portions and attachment means, the second expanding portion disposed between the first expanding portion and the proximal end of the anchoring member, the attachment means coupling the graft to the first expanding portion so that expansion of the first expanding portion causes the attachment means to pull the distal end of the graft over the second expanding portion; and
   d) means on the delivery base for expanding the anchoring member.

2. The graft delivery system of claim 1 wherein the attachment means comprises a plurality of staples radially disposed around the anchoring member having means for engaging the graft.

3. The graft delivery system of claim 2 wherein the means for engaging the graft comprise hooks or T-bars.

4. The graft delivery system of claim 1 wherein the first expanding portion comprises a plurality of sinusoidal circular expanding members.

5. The graft delivery system of claim 1 wherein the anchoring member is configured so that the distal end expands before the proximal end.

6. The graft delivery system of claim 1 wherein the means for expanding the anchoring member expands the distal end of the anchoring member before the proximal end.

7. The graft delivery system of claim 1 wherein the means for expanding comprises an inflatable balloon, and an inflation lumen extending through the elongated shaft in fluid communication with the interior of the inflatable balloon and the inflation lumen.

8. The graft delivery system of claim 1 wherein the diameter of the delivery base is from about 1.1 to about 4.0 times greater than the diameter of the elongated shaft.

9. A kit for deploying a graft to repair a portion of a patient's aorta comprising:
   a) a delivery catheter comprising a catheter having an elongated shaft, a delivery base on a distal portion of the elongated shaft and means for deploying the graft within the aorta;
   b) an aortic graft having proximal and distal ends and configured to be disposed about the elongated shaft when in a compressed state; and
   c) an anchoring member configured to be disposed on the delivery base, the anchoring member having proximal and distal ends, first and second expanding portions and attachment means, the second expanding portion disposed between the first expanding portion and the proximal end of the anchoring member, the attachment means configured to couple the aortic graft to the first expanding portion so that expansion of the first expanding portion causes the attachment means to pull the distal end of the aortic graft over the second expanding portion.

10. The kit of claim 9 wherein the deploying means comprises an inflatable balloon and an inflation lumen extending through the elongated shaft in fluid communication with the interior of the inflatable balloon and the inflation lumen.

11. The kit of claim 9 wherein the elongated shaft has a first outer diameter and the delivery base has a second outer diameter larger than the first outer diameter, the second outer being from about 1.1 to about 4.0 times greater than the diameter of the first outer diameter.

12. The kit of claim 9 wherein the attachment means comprises a plurality of staples radially disposed around the anchoring member having means for engaging the graft.

13. The kit of claim 12 wherein the means for engaging the graft comprise hooks or T-bars.

14. The kit of claim 9 wherein the first expanding portion comprises a sinusoidal circular expanding member.

* * * * *